(12) United States Patent
Jochum

(10) Patent No.: US 10,493,256 B2
(45) Date of Patent: Dec. 3, 2019

(54) PORT FOR A CATHETER

(71) Applicant: Fresenius Kabi Deutschland GMBH, Bad Homburg (DE)

(72) Inventor: Christoph Jochum, Nidderau (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 29 days.

(21) Appl. No.: 15/118,373

(22) PCT Filed: Feb. 3, 2015

(86) PCT No.: PCT/EP2015/052114
§ 371 (c)(1),
(2) Date: Aug. 11, 2016

(87) PCT Pub. No.: WO2015/132027
PCT Pub. Date: Sep. 11, 2015

(65) Prior Publication Data
US 2017/0165464 A1 Jun. 15, 2017

(30) Foreign Application Priority Data

Mar. 3, 2014 (EP) .................................... 14157404

(51) Int. Cl.
*A61M 39/02* (2006.01)
(52) U.S. Cl.
CPC . *A61M 39/0208* (2013.01); *A61M 2039/0223* (2013.01); *A61M 2039/0229* (2013.01)
(58) Field of Classification Search
CPC ...... A61M 39/0208; A61M 2039/0229; A61M 2039/0223; A61M 2039/0238;
(Continued)

(56) References Cited

U.S. PATENT DOCUMENTS 5,647,855 A 7/1997 Trooskin
6,478,783 B1 * 11/2002 Moorehead ....... A61M 5/14276
604/132

(Continued)

FOREIGN PATENT DOCUMENTS

EP         2098197 A1    9/2009
WO    WO2005/032645 A    4/2005
WO    WO2013/189918 A1   12/2013

OTHER PUBLICATIONS

International Search Report for International Application No. PCT/EP2015/052114, dated Apr. 2, 2015.

(Continued)

*Primary Examiner* — Emily L Schmidt
(74) *Attorney, Agent, or Firm* — Cook Alex Ltd.

(57) ABSTRACT

A port (1) for a catheter comprises: a housing (10) having a base plate (12); a cavity (140) arranged in the housing (10) for receiving a fluid; a membrane (13) attached to the housing (10) and arranged on an opening (102) of the housing (10) for sealing the opening (102) such that the cavity (140) is enclosed in the housing (10) in a fluid-tight manner; and a connector (15) for connecting a catheter (2) to the housing (10) to provide a fluid connection between the cavity (140) and the catheter (2). The port (1) has an outer shape defined by the housing (10) and the membrane (13) attached to the housing (10). In addition at least one adapter piece (3, 4) is provided, the at least one adapter piece (3, 4) in a preassembly state being separate from the housing (10) and being attachable to the housing (10) to alter the outer shape of the port (1), wherein the port (1) is operational with or without the at least one adapter piece (3, 4) attached to the housing (10). In this way a port is provided which in a uniform manner may be used with different patients.

15 Claims, 7 Drawing Sheets

(58) Field of Classification Search
CPC .. A61M 2039/0258; A61M 2039/0294; A61M 2039/0288; A61M 2039/0261
See application file for complete search history.

(56) References Cited

U.S. PATENT DOCUMENTS

| | | | | |
|---|---|---|---|---|
| 2004/0078004 | A1* | 4/2004 | Bourne | A61M 39/04 604/174 |
| 2007/0161958 | A1* | 7/2007 | Glenn | A61M 39/0208 604/175 |
| 2009/0137960 | A1* | 5/2009 | Johansson | A61M 39/0208 604/175 |
| 2009/0157106 | A1* | 6/2009 | Marcotte | A61F 5/0056 606/157 |
| 2011/0218392 | A1* | 9/2011 | Honaryar | A61M 39/0208 600/37 |
| 2011/0251453 | A1* | 10/2011 | Honaryar | A61F 5/0056 600/37 |
| 2012/0123342 | A1* | 5/2012 | Andrews | A61M 5/14276 604/175 |
| 2016/0015891 | A1 | 1/2016 | Papiorek | |

OTHER PUBLICATIONS

Written Opinion of the International Searching Authority for International Application No. PCT/EP2015/052114, dated Apr. 2, 2015.
Claims 1-15 from file history of U.S. Appl. No. 14/408,643—English version of claims 1-15 of WO 2013/189918 A1.

* cited by examiner

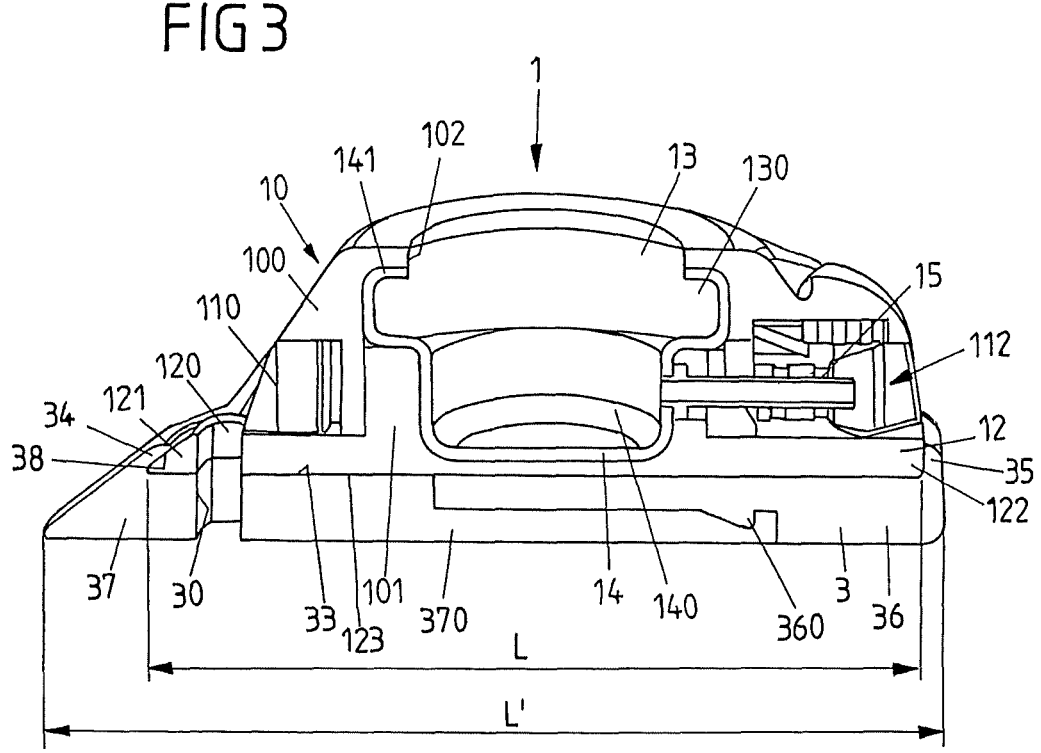

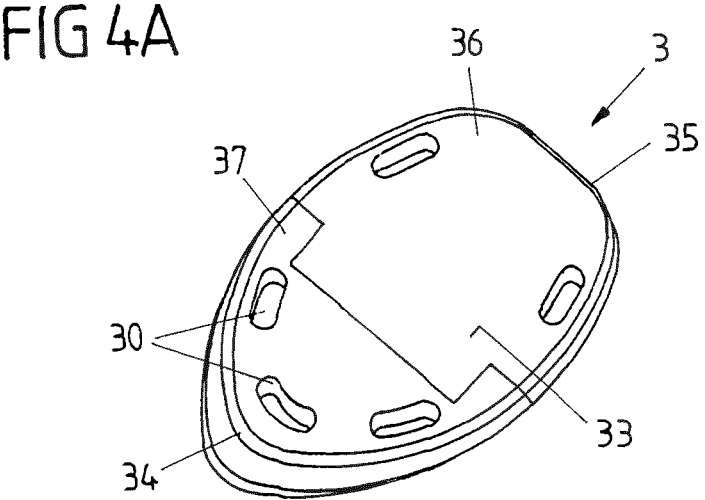
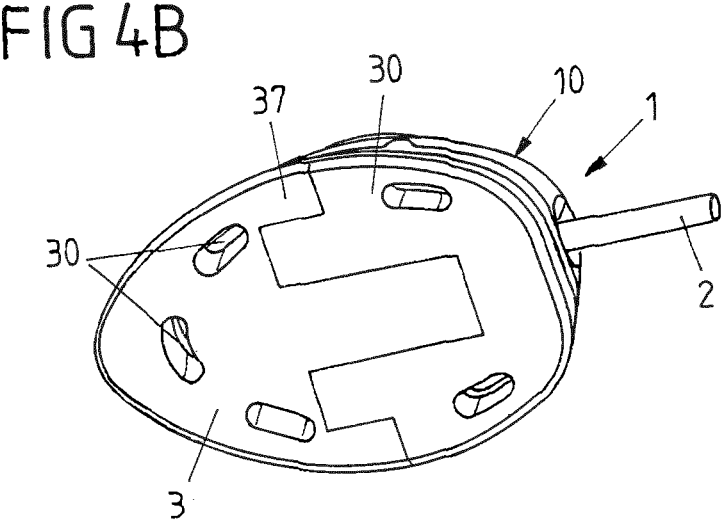

PORT FOR A CATHETER

The present application is the U.S. National Stage of PCT International Patent Application No. PCT/EP2015/052114, filed Feb. 3, 2015, which claims the benefit of and priority to European Patent Application No. 14157404.6, filed Mar. 3, 2014, the contents of both of which are hereby incorporated herein by reference.

The invention relates to a port for catheter according to the preamble of claim 1 and a construction set comprising a port for a catheter.

A port of this kind comprises a housing having a base plate, a cavity arranged in the housing for receiving a fluid, in particular a medical fluid such as a drug, a membrane attached to the housing and arranged on an opening of the housing for sealing the opening such that the cavity is enclosed in the housing in a fluid-tight manner, and a connector for connecting a catheter to the housing to provide a fluid connection between the cavity and the catheter. The port herein has an outer shape defined by the housing and the membrane attached to the housing.

A port of this kind, as it is known for example from EP 1 675 641 B1, can be implanted into a patient in that it for example is inserted subcutaneously beneath the skin of a patient. The port serves for infusing a medical drug, a blood product, a nutritional fluid or another medical fluid into the venous or arterial system of a patient. By means of the port a medical fluid can be given to a patient in a repeated fashion over a rather long period of time. Because the port is completely implanted under the skin of a patient, the risk for infections is reduced, and a medical fluid can be administered to the patient for treatment over a long period of time without the patient having to be stationary in a hospital and without the port impacting the everyday life of the patient.

During an infusion, a medical fluid is guided from the cavity enclosed in the housing via the connector to a catheter connected to the connector and via the catheter to a location of action in the patient, for example into the venous or arterial system of the patient. The catheter herein together with the port is implanted into the patient and is placed in the patient such that the medical fluid can be transported to the predefined location of action in the patient.

Dependent on the constitution of a patient it may be necessary to use ports of different shape. For example, a patient having a rather large body mass and body volume may require to use a rather large port. In contrast, a small patient having a small body mass and body volume may require the use of a small-sized port which can be subcutaneously implanted in a rather tight skin pocket of the patient. Hence, nowadays, different ports for different patients are used.

Such ports must be designed and produced separately from one another. Also, a hospital must order and keep on stock different ports. The use of such different ports hence adds to the costs both on the side of the manufacturer and on the side of a hospital or another treating entity.

It is an object of the instant invention to provide a port which in a uniform manner may be used with different patients.

This object is achieved by means of a port having the features of claim 1.

Accordingly, the port comprises at least one adapter piece, the at least one adapter piece in a preassembly state being separate from the housing and being attachable to the housing to alter the outer shape of the port, wherein the port is operational with or without the at least one adapter piece attached to the housing.

The instant invention starts from the idea to provide a port having a housing and a cavity arranged therein, which as such is operational and hence can be used and implanted into a patient for medical treatment. The housing of the port herein defines an outer shape of the port, which however may be altered by attaching one or multiple adapter pieces to the housing. By using one or multiple adapter pieces being attached to the housing the size of the port hence can be varied. The port can be used without any adapter pieces and as such has a rather small size. By attaching one or multiple adapter pieces to the housing of the port the size of the port can be increased and the port hence can be adapted for a specific use in a particular patient.

The at least one adapter piece may be releasably attachable to the housing of the port. An adapter piece may hence be attached to the housing and in an attached state is fixedly held on the housing, but may be detached from the housing again.

By providing one or multiple adapter pieces attachable to the housing a port system is provided which in a variable way can be used in different patients. A port having a rather small size may be provided by not attaching any adapter pieces to the housing. Such small port may be used in particular in small patients. To increase the size of the port one or multiple adapter pieces may be attached to the housing such that the outer shape of the port is altered and adapted in particular for use in bigger patients.

By means of such port a single port having a uniform structural built may be used in connection with a large variety of patients. Dependent on a particular patient the port by means of one or multiple adapter pieces may be adapted in its size and outer shape such that it can be fitted to the specific needs of the particular patient.

The outer shape of the port in particular is defined by a maximum height, a maximum length and a maximum width, wherein the maximum height is measured along a direction perpendicular to a plane of the extension of the base plate of the housing and the maximum length and the maximum width are measured in directions parallel to the plane of extension of the base plate. If no adapter piece is attached to the housing, the maximum length and the maximum width of the port herein may be defined by the extension of the base plate. The base plate herein is arranged on a side of the housing opposite the membrane and hence defines a bottom of the port.

In an advantageous embodiment the at least one adapter piece is attached to the base plate. In a mounted state the adapter piece preferably extends parallel to the base plate and is connected immediately to the base plate. The adapter piece hence adds to the height of the port and furthermore may have a larger length and/or width than the base plate, such that also the maximum length and/or maximum width of the port are increased.

By attaching one or multiple adapter pieces to the base plate, in particular the height of the port is increased. The adapter piece herein may have a different width and/or different length than the base plate such that by attaching one or multiple adapter pieces to the base plate the shape of the port in particular at its bottom may be adapted to fit the specific requirements of a patient.

In addition, it is conceivable that other adapter pieces can be attached to other faces of the housing such that the shape and size of the port may be adapted at other faces of the housing.

Herein, a user may choose between different adapter pieces. For example, a user may have the option to attach one or multiple adapter pieces to the base plate in order to increase the height of the port and in addition to attach one or multiple adapter pieces to other faces of the housing. Or the user may use only adapter pieces to be attached to other faces of the housing such that the height of the port is unchanged, but the general shape of the port is altered.

The port may have an insertion piece inserted into the housing and forming the cavity. The insertion piece may function as an inlay providing the cavity, wherein the insertion piece preferably is made of a material resistant against the medical fluid to be used in the port, for example a metallic material or a ceramic material. The insertion piece may also be formed such that it holds the membrane in a positive locking manner. For example, the insertion piece at its upper rim may have a groove-like shape into which the membrane is inserted in a positive locking manner.

The membrane serves as an access means for introducing a medical fluid into the cavity of the port. For this, a puncture needle may be used for puncturing the membrane such that a medical fluid through the membrane can be filled into the cavity of the port.

In a particular embodiment, a first adapter piece and a second adapter piece are provided to be used in connection with the housing of the port. Herein, the first adapter piece and the second adapter piece in the preassembly state are separate from the housing. The first adapter piece is attachable to the housing by attaching it to the base plate of the housing, and the second adapter piece is attachable to the first adapter piece. In a mounted stated, hence, the first adapter piece is firmly connected to the base plate and the second adapter piece is firmly connected to the first adapter piece. By using such adapter pieces the height of the port may be adapted to fit the specific requirements of a patient, wherein in addition the first adapter piece and/or the second adapter piece may have a length and/or width larger than the base plate of the port such that by using the adapter pieces the length and/or width of the port may be increased.

The object is also achieved by means of a construction set comprising a port for a catheter. The port comprises:
- a housing having a base plate,
- a cavity arranged in the housing for receiving a fluid,
- a membrane attached to the housing and arranged on an opening on the housing for sealing the opening such that the cavity is enclosed in the housing in a fluid-tight manner, and
- a connector for connecting a catheter to the housing to provide a fluid connection between the cavity and the catheter.

Herein, the port has an outer shape defined by the housing and the membrane attached to the housing. In addition, multiple different adapter pieces are provided which are attachable to the housing and/or to one another for altering the outer shape of the port, the multiple different adapter pieces in a preassembly state being separate from the housing, wherein the port is operational with or without the multiple different adapter pieces attached to the housing.

The advantages and advantageous embodiments of the port described above equally apply also to the construction set such that it shall be referred to the above.

In particular, by means of such a construction set a port in a variable fashion may be adapted to specific requirements in connection with different patients. The use of such a construction set allows providing a port system of a single kind which is delivered to for example a hospital and uniformly may be used in connection with a large variety of different patients. For this, a port which is functionally operable as such may be altered in its outer shape by using one or multiple adapter pieces in connection with the port.

The idea underlying the invention shall subsequently be described in more detail with respect to the embodiments shown in the figures. Herein:

FIG. 3 shows a sectional view along line A-A according to FIG. 2A;

FIG. 4A shows a separate view of an adapter piece to be attached to the base plate of the housing;

FIG. 4B shows the adapter piece attached to the base plate;

Figure 1A:
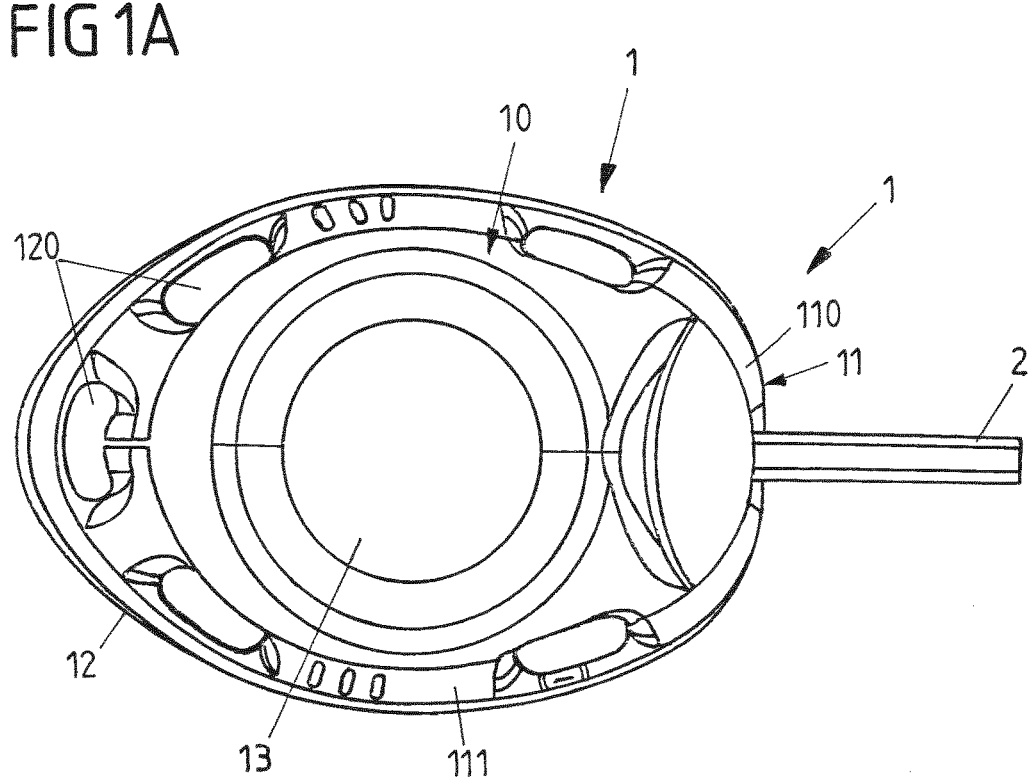
FIG. 1A shows a top view of a port.
Figure 1B:
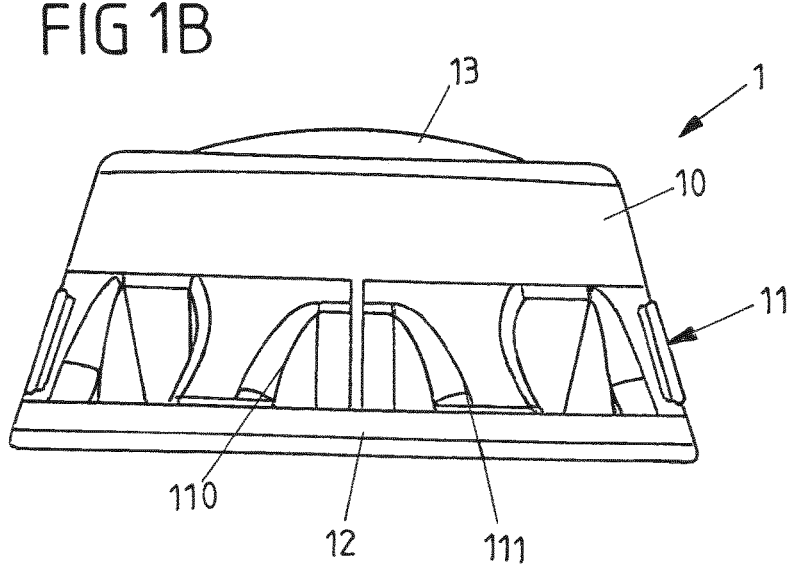
FIG. 1B shows a side view of the port of FIG. 1A.

FIGS. 1A and 1B show views of a port 1 having a housing 10 and a membrane 13 attached to the housing 10. A catheter 2 is arranged on the housing 10 and extends from the port 1, the catheter 2 being fixed to the housing 10 by means of a fixing device 11 having two clamping levers 110, 111 being pivotably arranged on the housing 10. At a side opposite to the membrane 13, the housing 10 comprises a base plate 12 which forms the bottom of the port 1.

The port 1 may be implanted subcutaneously under a skin of a patient. Herein, the port 1 is constituted to hold a medical fluid which via the catheter 2 attached to the housing 10 of the port 1 is to be administered to the patient, for example by guiding it into the venous or arterial system of the patient.

Figure 2A:
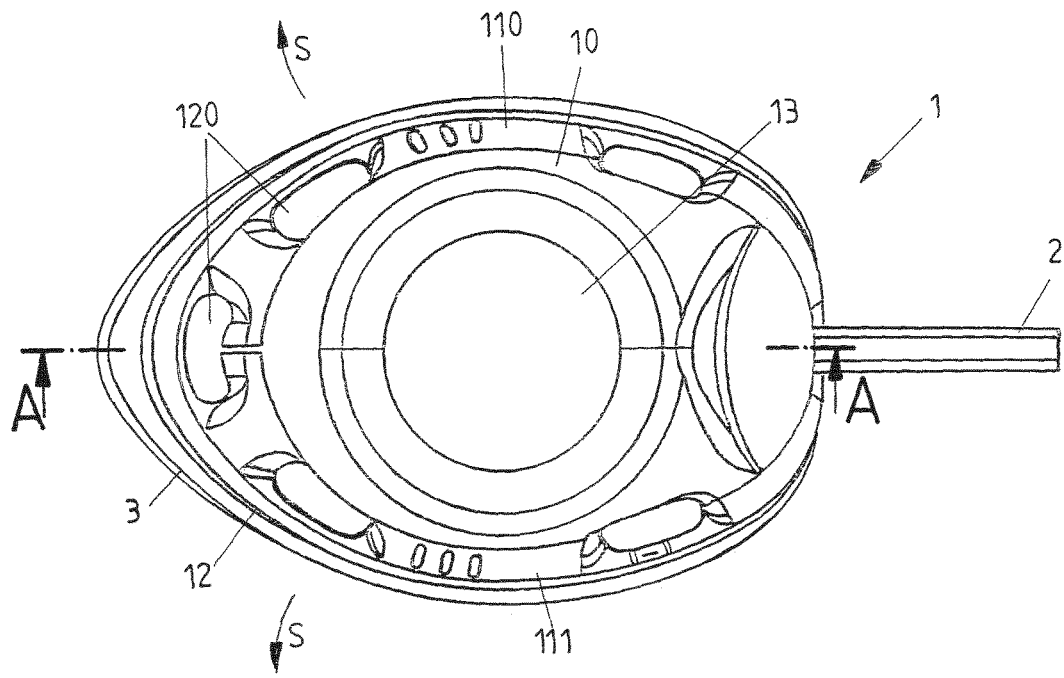
FIG. 2A shows a top view of the port according to FIG. 1A, with an adapter piece attached to a base plate of a housing of the port.
Figure 2B:
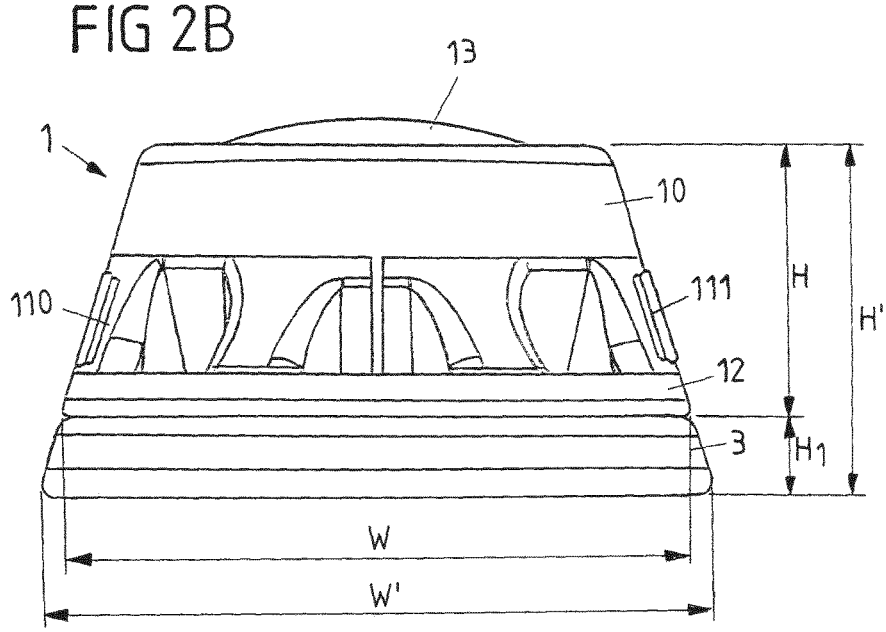
FIG. 2B shows a side view of the arrangement of FIG. 2A.

FIGS. 2A and 2B show the port 1 of FIGS. 1A and 1B, but with an adapter piece 3 attached to the base plate 12 of the housing 10 of the port 1. The adapter piece 3, for the operation of the port 1, has no immediate function, but serves to alter the outer shape of the port 1 in order to adapt the port 1 to specific requirements for implantation into a particular patient.

Namely, the port 1, without the adapter piece 3 attached, has a maximum width W and a maximum length L (see FIG. 3) defined by the extension of the base plate 12. In addition, the port 1 has a height H defined by the height of the housing 12. By attaching the adapter piece 3 to the base plate 12 of the housing 10, the width W' as well as the length L' and the height H' of the port 1 are increased such that the port 1 has a larger overall size and in this way is adapted for use for example in a bigger patient.

As shown in FIG. 2B, the housing 10 has a height H, whereas the adapter piece 3 has a height H1. By attaching the adapter piece 3 to the base plate 12 of the housing 10, hence, the overall height H' of the port 1 is increased.

By means of one or multiple different adapter pieces 3, hence, a functional port module which as such is operational and is shown in FIGS. 1A and 1B can be used in connection with a large variety of different patients. By means of adapter pieces 3 the port 1 may be adapted to the specific requirements of a patient. Hence, there is no need for different ports as such, but one uniform port 1 may be used and adapted for different patients.

The functional setup of the port 1 is shown in FIG. 3. Namely, the housing 10 comprises a first housing part 100 and a second housing part 101 attached to each other. The base plate 12 is formed on the second housing part 101, whereas the first housing part 100 defines an opening 102 in which the membrane 13 is held.

The housing parts 100, 101 together form a cavity 140 for holding a medical fluid. In-between the housing parts 100, 101 an insertion piece 14 is inserted which defines the cavity 140 and which, at an end section 141 at its upper rim holds a circumferential edge 130 of the membrane 13 in a positive locking manner. The membrane 13 hence is firmly attached to the insertion piece 14, which preferably is made of a material resistant to a medical fluid to be inserted into the cavity 140, for example a metallic or ceramic material.

The membrane 13 may be punctured by a puncture needle such that, via the puncture needle, a medical fluid may be inserted into the cavity 140. Through the membrane 13, hence, in an implanted state of the port 1, the cavity 140 may be refilled by introducing a medical fluid into the cavity 140, such that the port 1 may be used over a long period of time within a patient.

The port 1 comprises a fixing device 11 having two clamping levers 110, 111 which are pivotably arranged on the housing 10 and may be pivoted with respect to the housing 10 along a pivoting direction S. In a pivoted state in which the clamping levers 110, 111 are pivoted out and extend from the housing 10 the catheter 2 can be inserted into an opening 112 and placed on a connector 15, which is attached to the second housing part 101 and is in fluid connection with the cavity 140. By pivoting the clamping levers 110, 111 in and bringing them into the position shown in FIGS. 1A and 2A, the catheter 2 is clamped to the connector 15 and hence firmly fixed to the connector 15 such that it cannot be removed from the connector 15 without further ado.

Figure 5A:
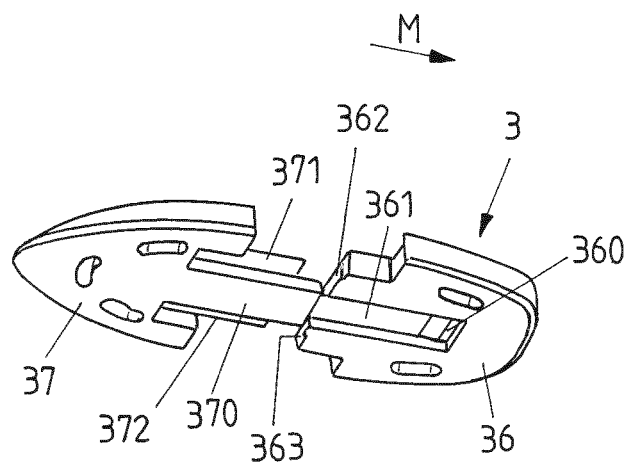
FIG. 5A shows the adapter piece of FIG. 4A, the adapter piece being assembled of two parts.
Figure 5B:
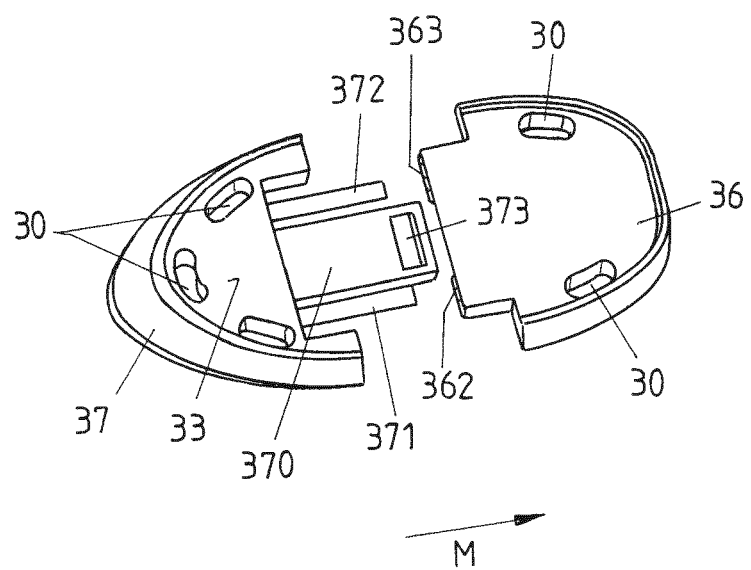
FIG. 5B shows another view of the adapter piece of FIG. 5A.

The adapter piece 3 of the embodiment of FIGS. 2A, 2B and 3 is in further views shown in FIGS. 4A, 4B and 5A, 5B. The adapter piece 3 is made up of two parts 36, 37 which are connected to each other by slidingly placing the parts 36, 37 on each other in a mounting direction M, as indicated in FIGS. 5A and 5B.

For connecting the parts 36, 37 to each other, part 37 comprises a locking finger 370 extending along the mounting direction M towards the other part 36. Part 37 furthermore comprises two pins 371, 372 extending in parallel to the locking finger 370. For connecting the parts 36, 37 to each other, the locking finger 370 is inserted into a groove-like indentation 361 on the bottom of the part 36 until an indentation 373 on the locking finger 370 snaps into engagement with a locking element 360 in the shape of a protrusion within the indentation 361 of the part 36. While sliding the locking finger 370 in the mounting direction M into the groove-like indentation 361, also the pins 371, 372 are inserted into corresponding reception openings 362, 363 in the part 36, such that by means of the locking finger 370 snappingly engaging the locking element 360 and the pins 371, 372 being inserted into the reception openings 362, 363 the parts 36, 37 are firmly connected to each other in a mounted state, as shown in FIG. 4A.

The parts 36, 37 together define a surface 33 which, in a state attached to the base plate 12, faces a bottom face 123 of the base plate 12, as shown in FIG. 3. Herein, on the face 33 holes 30 are defined which are congruent to the fixing holes 120 of the base plate 12 such that a yarn may be inserted through the fixing holes 120 and the holes 30 for fixing the port 1 within a patient.

The adapter piece 3, on the part 37, has a front edge 34 serving as a connection member and defining a connection surface 38 (FIG. 3) and a recess into which a front end 121 of the base plate 12 can be inserted in a positive locking manner, as shown in FIG. 3. At the part 36 a back edge 35 is defined, which in the attached state faces a back edge 122 of the base plate 12. In the attached state, shown in FIG. 3, hence, the adapter piece 3 in a positive locking manner is held on the base plate 12 such that the adapter piece 3 is firmly fixed to the housing 10 of the port 1.

Figure 6A:
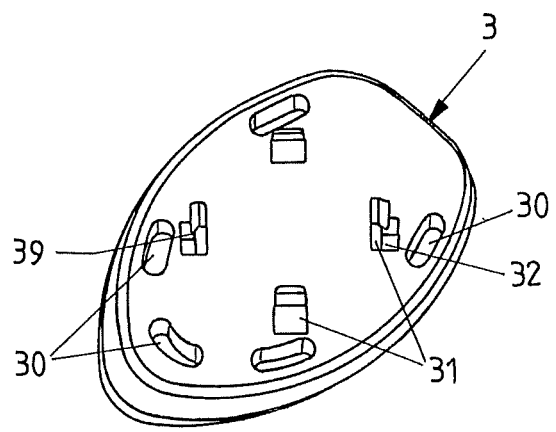
FIG. 6A shows a separate view of another embodiment of an adapter piece to be attached to the base plate of the port.
Figure 6B:
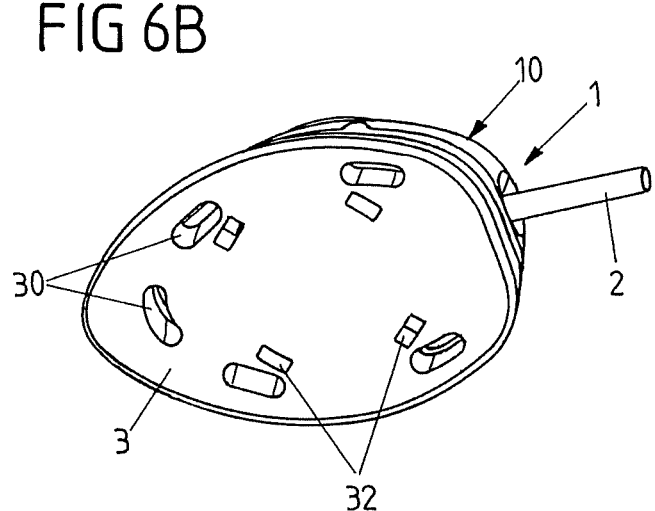
FIG. 6B shows the adapter piece attached to the base plate of the housing of the port.

FIGS. 6A and 6B show views of another embodiment of an adapter piece 3 which may be attached to the base plate 12 of the housing 10 of the port 1. The adapter piece 3, in this case, is made of one piece and comprises locking elements 31 which, for connecting the adapter piece 3 to the base plate 12 of the housing 10, can be inserted into corresponding locking openings on the base plate 12. FIG. 6B shows the adapter piece 3 in a state in which it is attached to the base plate 12 of the housing 10 of the port 1.

In the vicinity of the locking elements 31, which serve as connection members, openings 32 are arranged in the adapter piece 3. The connection members 31 each feature a connection surface 39 (FIG. 6A) that opposes a corresponding opening 32. Through such openings 32 a tool may be inserted to act onto the locking elements 31 for releasing the adapter piece 3 from the base plate 12. The adapter piece 3 hence may be released from the base plate 12.

Figure 7A:
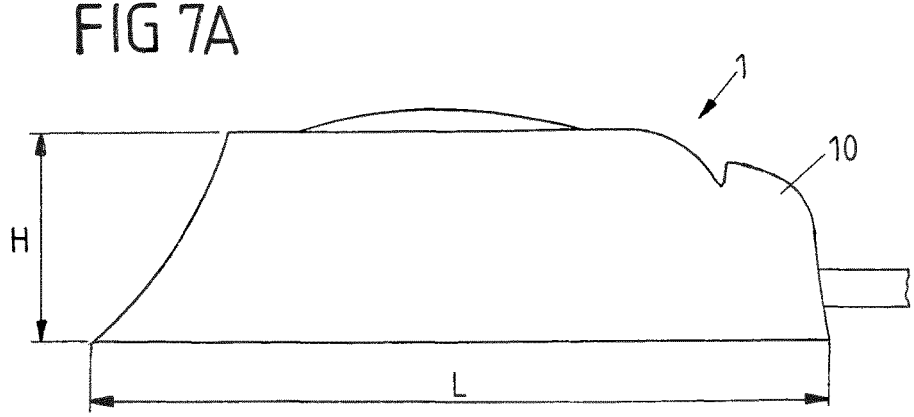
FIG. 7A shows a schematic view of a port, with no adapter pieces attached to the housing of the port.
Figure 7B:
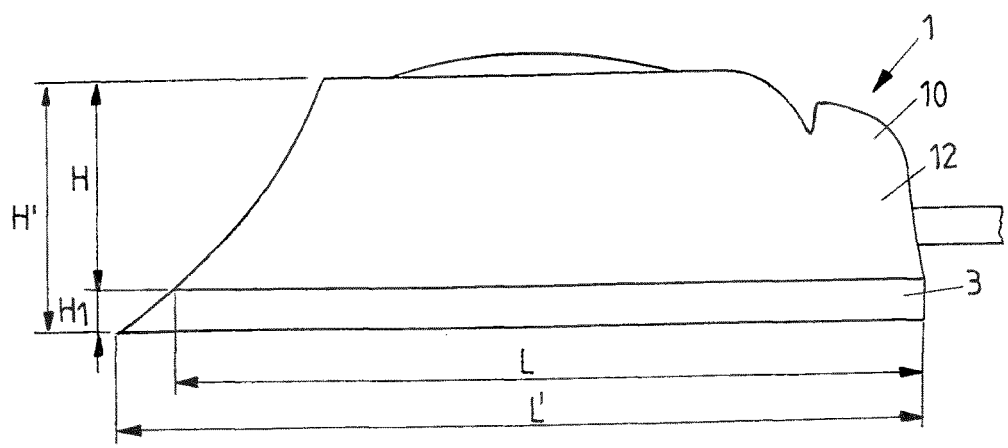
FIG. 7B shows the port, with one adapter piece attached to the base plate of the housing of the port.
Figure 7C:
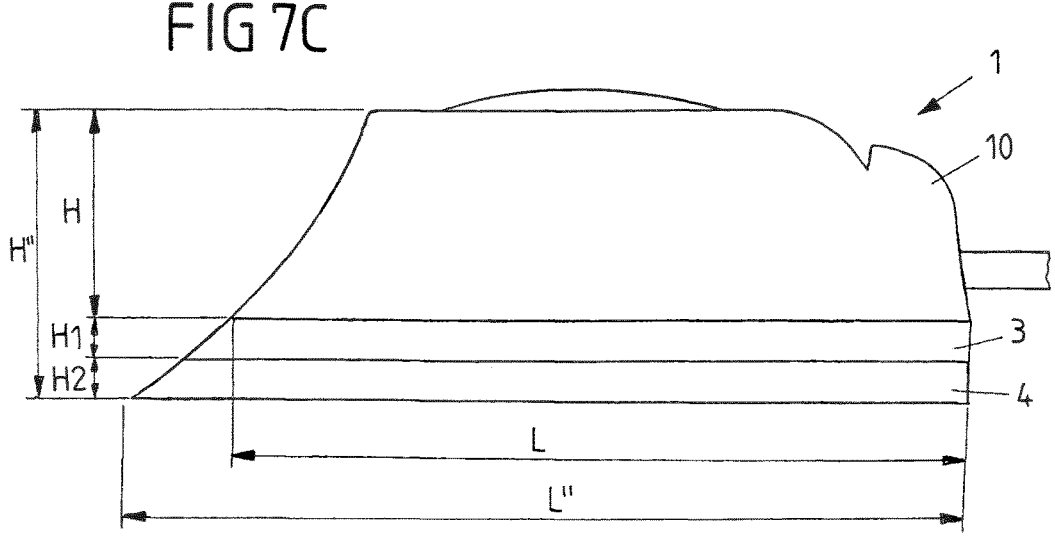
FIG. 7C shows the port with two adapter pieces attached.

As shown in the schematic drawings of FIG. 7A to 7C, the port 1 may be used in connection with no adapter piece (FIG. 7A), with one adapter piece 3 (FIG. 7B) or with two adapter pieces 3, 4 (FIG. 7C), wherein it is also conceivable to use even more than two adapter pieces 3, 4 or other adapter pieces than the ones shown. As shown in FIG. 7A to 7C, by attaching one or multiple adapter pieces 3, 4 to the housing 10 of the port 1, the outer shape of the port 1 may be altered to adapt the port 1 for use in different patients. Namely, the housing 10 as such may define an overall height H and overall length L of the port 1, as shown in FIG. 7A. By attaching one adapter piece 3 to the base plate 12 of the housing 10, the overall height H' and the overall length L' of the port 1 may be increased. By attaching a second adapter piece 4 to the first adapter piece 3 as shown in FIG. 7C, the overall height H" and the overall length L" of the port 1 may further be increased, such that the port 1 in a variable fashion may be adapted for use in different patients.

The idea underlying the invention is not limited to the embodiments described above, but may be implemented also in a rather different fashion.

For example, adapter pieces may be provided which can be attached to other faces of the housing than the base plate.

In addition, adapter pieces of different shape and size may be provided which can be used in an alternative fashion such that either one adapter piece or another adapter piece may be used. In this way, a variable construction set may be provided which may allow for adapting a port variably for different needs, while the port as such in its functional built stays the same, but can be adapted in its outer shape by using one or multiple adapter pieces in connection with the housing of the port.

LIST OF REFERENCE NUMERALS

1 Port
10 Housing 100, 101 Housing part
102 Opening
11 Fixing device
110, 111 Clamping levers
112 Opening
12 Base plate
120 Fixing holes
121 Front edge
122 Back edge
123 Outer face
13 Membrane
130 Edge
14 Insertion piece (trough)
140 Cavity
141 End section
15 Connector
2 Catheter
3 Adapter piece
30 Holes
31 Locking elements
32 Openings
33 Surface
34 Front edge
35 Back edge
36 Part
360 Locking element
361 Indentations
362, 363 Reception opening (channel)
37 Part
370 Locking finger
371, 372 Pin
373 Indentation
4 Adapter piece
H, H', H", H1, H2 Height
L, L', L" Length
M Mounting direction
S Pivoting direction
W, W' Width

The invention claimed is:

1. A port for a catheter, comprising:
   a housing having a base plate, wherein the base plate includes a plurality of base plate fixing holes and a base plate width and a base plate length defining a base plate outer perimeter,
   a cavity arranged in the housing for receiving a fluid,
   a membrane attached to the housing and arranged on an opening of the housing for sealing the opening such that the cavity is enclosed in the housing in a fluid-tight manner, and
   a connector for connecting a catheter to the housing to provide a fluid connection between the cavity and the catheter,
   wherein the base plate is arranged on a side of the housing opposite the membrane and the port has an outer shape defined by the housing and the membrane attached to the housing,
   characterized by
   at least one adapter piece having a plurality of adapter piece fixing holes and an adapter piece width and an adapter piece length defining an adapter piece outer perimeter wherein the adapter piece width is greater than the base plate width or the adapter piece length is greater than the base plate length so that the adapter piece outer perimeter is greater than the base plate outer perimeter, the at least one adapter piece in a preassembly state being separate from the housing of the port after the port is assembled and being releasably attachable to the housing of the port after the port is assembled to alter the outer shape of the port, wherein the port is operational with or without the at least one adapter piece attached to the housing, wherein the at least one adapter piece in a mounted state is connected to the base plate such that the plurality of adapter piece fixing holes is congruent to the plurality of base plate fixing holes whereby the port may be fixed within a patient and the at least one adapter piece is fixedly held on the housing by a positive locking connection and extends parallel to the base plate, said positive locking connection including a connection member having a connection surface that is:
   i) positioned in a spaced and opposing relationship with a top surface of the at least one adapter piece; and
   ii) configured to be moved parallel to the base plate to engage the base plate and to place the at least one adapter piece in the mounted state.

2. The port according to claim 1, characterized in that the outer shape is defined by a maximum height, a maximum length and a maximum width, wherein the maximum height is measured along a direction perpendicular to a plane of extension of the base plate and the maximum length and the maximum width are measured in directions parallel to the plane of extension of the base plate.

3. The port according to claim 2, characterized in that the maximum length and the maximum width are defined by the extension of the base plate.

4. The port according to claim 1, characterized in that the at least one adapter piece is attached to the base plate.

5. The port according to claim 1, characterized in that an insertion piece is arranged in the housing and forms the cavity.

6. The port according to claim 5, characterized in that the membrane is attached to the insertion piece in a positive locking manner.

7. The port according to claim 1, characterized in that a first adapter piece is attachable to the housing, and a second adapter piece is attachable to the first adapter piece.

8. The port according to claim 7, characterized in that in a mounted state the first adapter piece is attached to the base plate of the housing and the second adapter piece is attached to the first adapter piece.

9. The port according to claim 1 wherein the adapter piece width is greater than the base plate width and the adapter piece length is greater than the base plate length.

10. The port according to claim 1 wherein the at least one adapter piece is rigid.

11. The port according to claim 1 wherein the housing includes a sidewall positioned between the base plate and the membrane and wherein the fluid connection between the cavity and the catheter provided by the connector passes through the sidewall.

12. A construction set, comprising a port for a catheter, the port comprising:
   a housing having a base plate, wherein the base plate includes a plurality of base plate fixing holes and a base plate width and a base plate length defining a base plate outer perimeter,
   a cavity arranged in the housing for receiving a fluid,
   a membrane attached to the housing and arranged on an opening of the housing for sealing the opening such that the cavity is enclosed in the housing in a fluid-tight manner, and
   a connector for connecting a catheter to the housing to provide a fluid connection between the cavity and the catheter, wherein the port has an outer shape defined by the housing and the membrane attached to the housing, characterized by multiple different adapter pieces, each adapter piece having a plurality of adapter piece fixing holes and an adapter piece width and an adapter piece length defining an adapter piece outer perimeter and wherein the adapter piece width is greater than the base plate width or the adapter piece length is greater than the base plate length so that the adapter piece outer perimeter is greater than the base plate outer perimeter and each adapter piece being releasably attachable to at least one of the housing of the port after the port is assembled and another adapter piece for altering the outer shape of the port, the multiple different adapter pieces in a preassembly state being separate from the housing of the port after the port is assembled, wherein the port is operational with or without the multiple different adapter pieces attached to the housing, and wherein at least one of the multiple different adapter pieces in a mounted state is connected to the base plate such that the plurality of adapter piece fixing holes is congruent to the plurality of base plate fixing holes whereby the port may be fixed within a patient and the at least one of the multiple different adapter pieces is fixedly held on the housing by a positive locking connection and extends parallel to the base plate, said positive locking connection including a connection member having a connection surface that is:

i) positioned in a spaced and opposing relationship with a top surface of the at least one of the multiple different adapter pieces; and ii) configured to be moved parallel to the base plate to engage the base plate and to place the at least one of the multiple different adapter pieces in the mounted state.

13. The construction set according to claim 12 wherein the adapter piece width is greater than the base plate width and the adapter piece length is greater than the base plate length.

14. The construction set according to claim 12 wherein each adapter piece of the multiple different adapter pieces is rigid.

15. The construction set according to claim 12 wherein the housing includes a sidewall positioned between the base plate and the membrane and wherein the fluid connection between the cavity and the catheter provided by the connector passes through the sidewall.

* * * * *